United States Patent
Sgroi, Jr.

(10) Patent No.: US 11,331,782 B2
(45) Date of Patent: May 17, 2022

(54) RELOAD ASSEMBLY FOR A CIRCULAR STAPLING DEVICE

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 164 days.

(21) Appl. No.: 16/788,541

(22) Filed: Feb. 12, 2020

(65) Prior Publication Data

US 2020/0276693 A1 Sep. 3, 2020

Related U.S. Application Data

(60) Provisional application No. 62/812,681, filed on Mar. 1, 2019.

(51) Int. Cl.
*B25C 5/16* (2006.01)

(52) U.S. Cl.
CPC .......... *B25C 5/1696* (2013.01); *B25C 5/1617* (2013.01); *B25C 5/1679* (2013.01)

(58) Field of Classification Search
CPC ............ A61B 17/068; A61B 17/07214; A61B 17/07285; A61B 17/115; A61B 17/1155; A61B 17/1157; B25C 5/1617; B25C 5/1679; B25C 5/1696
USPC .................................. 227/175.1, 175.2, 120
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev et al. | |
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |

(Continued)

FOREIGN PATENT DOCUMENTS

| CA | 908529 A | 8/1972 |
|---|---|---|
| CA | 2805365 A1 | 8/2013 |

(Continued)

OTHER PUBLICATIONS

European Search Report dated Jun. 22, 2020, issued in EP Appln. No. 20160183, 8 pages.

*Primary Examiner* — Chelsea E Stinson

(57) ABSTRACT

A reload assembly includes a shell housing, a knife carrier, and a one-way collar. The knife carrier is movably positioned about an inner housing portion of the shell housing between retracted and advanced positions and supports a snap-ring. The one-way collar is movably supported about the inner housing portion of the shell housing from a retracted position to an advanced position in response to movement of the knife carrier from its retracted position to its advanced position. The snap-ring is movable with the knife carrier to a position proximally of the one-way collar when the one-way collar is in its advanced position to obstruct movement of the knife carrier back towards its advanced position.

20 Claims, 9 Drawing Sheets

(56) References Cited

U.S. PATENT DOCUMENTS

| | | |
|---|---|---|
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |

(56) References Cited

U.S. PATENT DOCUMENTS

| | | |
|---|---|---|
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2* | 12/2007 | Milliman ............ A61B 17/115 227/175.1 |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |

(56) References Cited

U.S. PATENT DOCUMENTS

| | | |
|---|---|---|
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,010,605 B2 * | 4/2015 | Olson ............... A61B 17/1155 227/175.1 |
| 9,351,724 B2 * | 5/2016 | Penna ............... A61B 17/1155 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |

(56) References Cited

U.S. PATENT DOCUMENTS

| | | |
|---|---|---|
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2021/0016426 A1* | 1/2021 | Sgroi, Jr. .............. B25C 5/1686 |

FOREIGN PATENT DOCUMENTS

| | | | |
|---|---|---|---|
| DE | 1057729 B | 5/1959 | |
| DE | 3301713 A1 | 7/1984 | |
| EP | 0152382 A2 | 8/1985 | |
| EP | 0173451 A1 | 3/1986 | |
| EP | 0190022 A2 | 8/1986 | |
| EP | 0282157 A1 | 9/1988 | |
| EP | 0503689 A2 | 9/1992 | |
| EP | 1354560 A2 | 10/2003 | |
| EP | 2138118 A2 | 12/2009 | |
| EP | 2168510 A1 | 3/2010 | |
| EP | 2238926 A2 | 10/2010 | |
| EP | 2524656 A2 | 11/2012 | |
| EP | 2614784 A2 | 7/2013 | |
| EP | 2614785 A2 | 7/2013 | |
| EP | 2730238 A1 | 5/2014 | |
| EP | 2754398 A2 | 7/2014 | |
| EP | 2962648 A1 | 1/2016 | |
| EP | 3701886 A1 * | 9/2020 | ......... A61B 17/1155 |
| FR | 1136020 A | 5/1957 | |
| FR | 1461464 A | 2/1966 | |
| FR | 1588250 A | 4/1970 | |
| FR | 2443239 A1 | 7/1980 | |
| GB | 1185292 A | 3/1970 | |
| GB | 2016991 A | 9/1979 | |
| GB | 2070499 A | 9/1981 | |
| JP | 2004147969 A | 5/2004 | |
| JP | 2013138860 A | 7/2013 | |
| NL | 7711347 A | 4/1979 | |
| SU | 1509052 A1 | 9/1989 | |
| WO | 8706448 A1 | 11/1987 | |
| WO | 8900406 A1 | 1/1989 | |
| WO | 9006085 A1 | 6/1990 | |
| WO | 98/35614 A1 | 8/1998 | |
| WO | 0154594 A1 | 8/2001 | |
| WO | 2008107918 A1 | 9/2008 | |

* cited by examiner

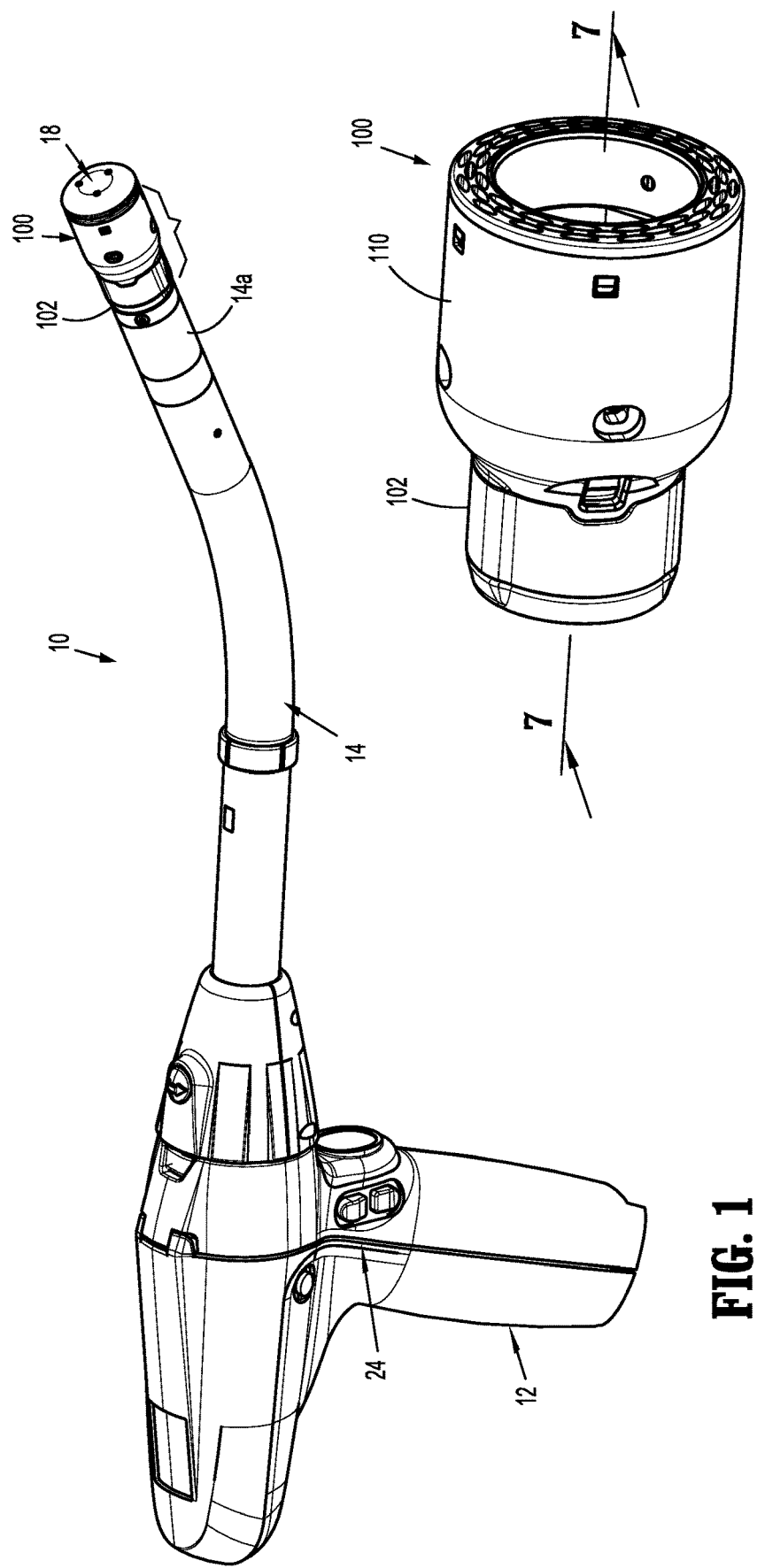

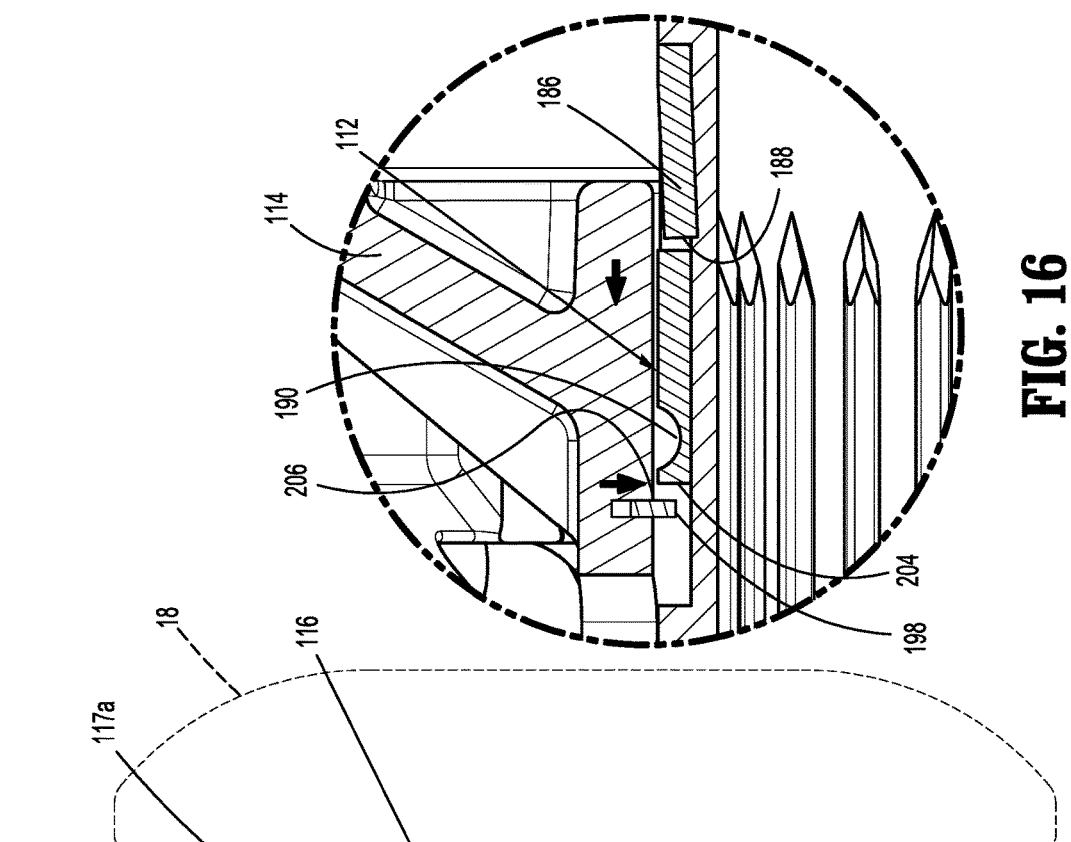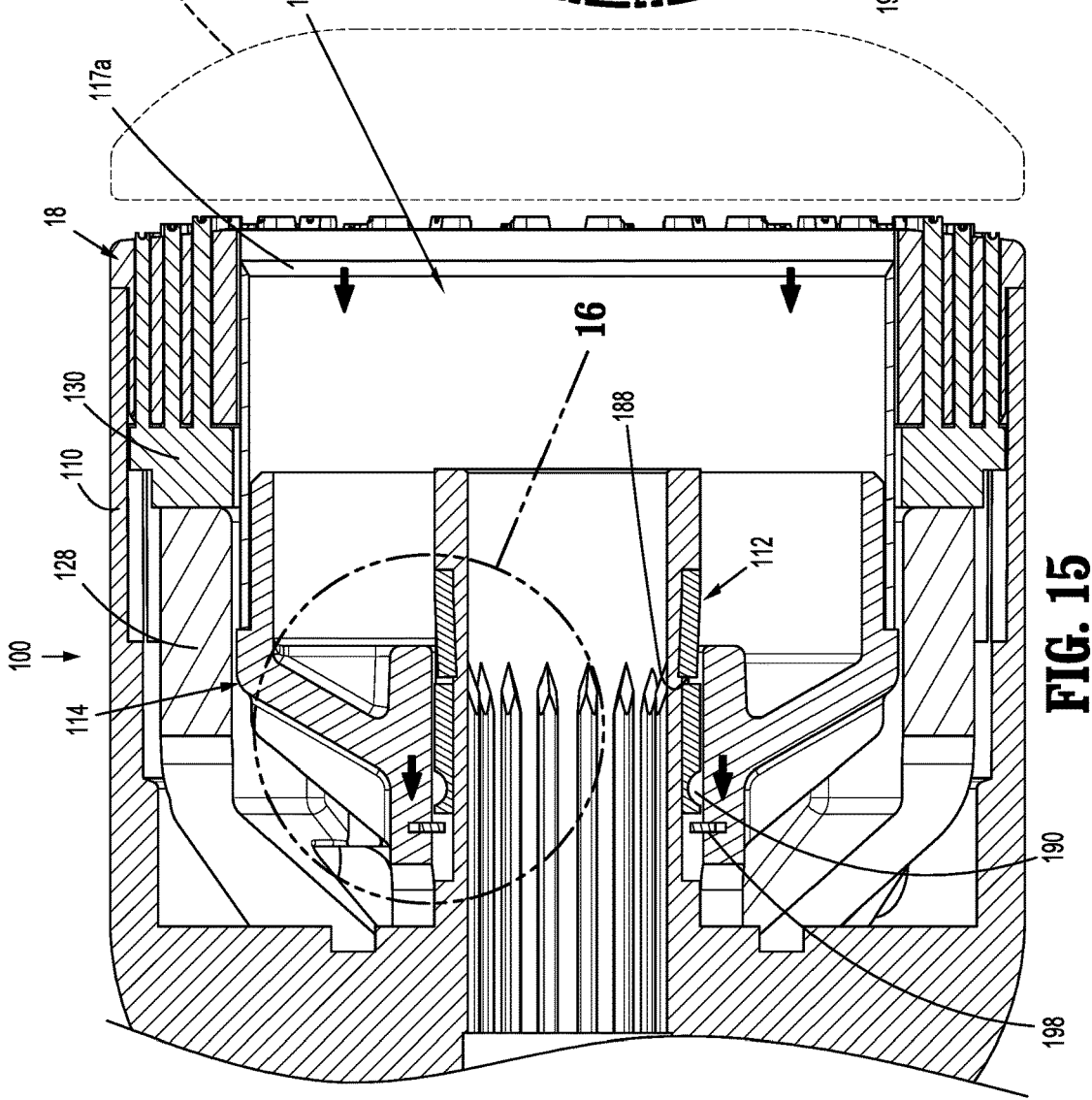

RELOAD ASSEMBLY FOR A CIRCULAR STAPLING DEVICE

CROSS-REFERENCE TO RELATED APPLICATIONS

This application claims the benefit of and priority to U.S. Provisional Patent Application Ser. No. 62/812,681 filed Mar. 1, 2019, the entire disclosure of which is incorporated by reference herein.

BACKGROUND

1. Technical Description

The present disclosure is directed to circular stapling devices and, more particularly, to reload assemblies for circular stapling devices with structure to retain a knife carrier in a retracted position after the stapling device is fired.

2. Background of Related Art

Conventional circular stapling devices include an elongate body and a shell or reload assembly that is supported on a distal portion of the elongate body. The reload assembly includes a shell housing, a staple cartridge supported on the shell housing having a plurality of staples, a pusher assembly, a knife defining a cylindrical cavity, and a knife carrier that supports the knife. The pusher assembly includes an annular pusher and a staple pushing member that is engaged with the annular pusher and is movable to move the staple pushing member to eject staples from the staple cartridge. The knife carrier is movable to advance the knife through the staple cartridge to core tissue After a stapling device has been operated to staple and cut tissue, the knife carrier and the knife are retracted to withdraw the knife into the shell housing. This serves two purposes. The first purpose is to move the knife to a position to allow removal of a tissue donut from within the cavity defined by the knife. The second purpose is to position the knife in a location recessed within the shell housing to avoid injury to a clinician during manipulation and disposal of the reload assembly.

In some instances, the tissue donut is compressed within the cavity defined by the knife to such a degree that removal of the tissue donut from within the cavity defined by the knife is difficult. A continuing need exists in the art for a reload assembly that includes improved structure for retaining the knife/knife carrier in a retracted position.

SUMMARY

One aspect of the present disclosure is directed to a reload assembly including a shell housing, a staple cartridge, a pusher, a knife carrier, and a one-way collar. The shell housing includes an inner housing portion and an outer housing portion. The inner housing portion has an outer surface defining an annular recess. The staple cartridge is supported on a distal portion of the shell housing. The staple cartridge has a plurality of staple pockets, each receiving a staple. The pusher is supported within the annular recess and is movable between a retracted position and an advanced position to eject the staples from the staple cartridge. The knife carrier includes a body defining a longitudinal axis and supporting a knife. The body of the knife carrier defines a central bore. The inner housing portion of the shell housing is positioned within the central bore of the knife carrier such that the knife carrier is movable about the inner housing portion of the shell housing between advanced and retracted positions. A resilient snap-ring is axially fixed within the central bore of the knife carrier. The one-way collar is movable within the annular recess of the inner housing portion of the shell housing from a retracted position to an advanced position in response to movement of the knife carrier from its advanced position to its retracted position. The snap-ring is movable to a position proximally of the one-way collar when the one-way collar is in its advanced position to obstruct movement of the knife carrier back towards its advanced position.

Another aspect of the present disclosure is directed to a circular stapling device including an elongate body, and a reload assembly. The elongate body has a proximal portion and a distal portion. The reload assembly is supported on the distal portion of the elongate body and includes a shell housing, a staple cartridge, a pusher, a knife carrier, and a one-way collar. The shell housing includes an inner housing portion and an outer housing portion. The inner housing portion has an outer surface defining an annular recess. The staple cartridge is supported on a distal portion of the shell housing. The staple cartridge has a plurality of staple pockets, each receiving a staple. The pusher is supported within the annular recess and is movable between a retracted position and an advanced position to eject the staples from the staple cartridge. The knife carrier includes a body defining a longitudinal axis and supporting a knife. The body of the knife carrier defines a central bore. The inner housing portion of the shell housing is positioned within the central bore of the knife carrier such that the knife carrier is movable about the inner housing portion of the shell housing between advanced and retracted positions. A resilient snap-ring is axially fixed within the central bore of the knife carrier. The one-way collar is movable within the annular recess of the inner housing portion of the shell housing from a retracted position to an advanced position in response to movement of the knife carrier from its advanced position to its retracted position. The snap-ring is movable to a position proximally of the one-way collar when the one-way collar is in its advanced position to obstruct movement of the knife carrier back towards its advanced position.

In embodiments, the one-way collar has an outer surface defining a retention groove and the resilient snap-ring is received within the retention groove when the knife carrier and the one-way collar are in their retracted positions.

In some embodiments, engagement between the snap-ring and the one-way collar causes movement of the one-way collar from its retracted position to its advanced position when the knife carrier moves from its advanced position to its retracted position.

In certain embodiments, the retention groove has a semi-circular configuration.

In embodiments, the one-way collar includes a body having at least one directional tang that is configured to prevent proximal movement of the one-way collar about the inner housing portion of the shell housing.

In some embodiments, each of the at least one directional tangs includes a cantilevered arm having a distal end secured to the body of the one-way collar.

In certain embodiments, the one-way collar defines a through bore and the cantilevered arm of each of the at least one directional tangs includes a proximal edge that is biased towards the through bore of the one-way collar into engagement with the inner housing portion of the shell housing.

In embodiments, the at least one directional tang includes a plurality of directional tangs.

In some embodiments, the annular recess has a proximal end and a distal end and the inner housing portion of the shell housing defines a stop surface at the distal end of the annular recess, wherein the stop member is positioned to engage the one-way collar to prevent movement of the one-way collar distally of the stop surface.

In certain embodiments, the one-way collar includes a proximal end defining a stop surface that is positioned to engage the snap-ring when the one-way collar is in an advanced position and the knife carrier is in its retracted position to prevent readvancement of the knife carrier.

In embodiments, the circular stapling device includes a handle assembly.

In some embodiments, the elongate body is adapted to be coupled to a robotically controlled surgical system.

BRIEF DESCRIPTION OF THE DRAWINGS

Various embodiments of the presently disclosed reload assembly are described herein below with reference to the drawings, wherein:

FIG. 1 is a side perspective view of a circular stapling device including an exemplary embodiment of the presently disclosed reload assembly in accordance with the present disclosure;

FIG. 2 is a side perspective view of the reload assembly of FIG. 1;

FIG. 15 is a side cross-sectional view of the reload assembly with the knife carrier and the knife in the retracted positions after the firing stroke of the reload assembly; and FIG. 16 is an enlarged view of the indicated area of detail shown in FIG. 16 with the reload assembly in a post-fired position.

DETAILED DESCRIPTION OF EMBODIMENTS

Figure 3:
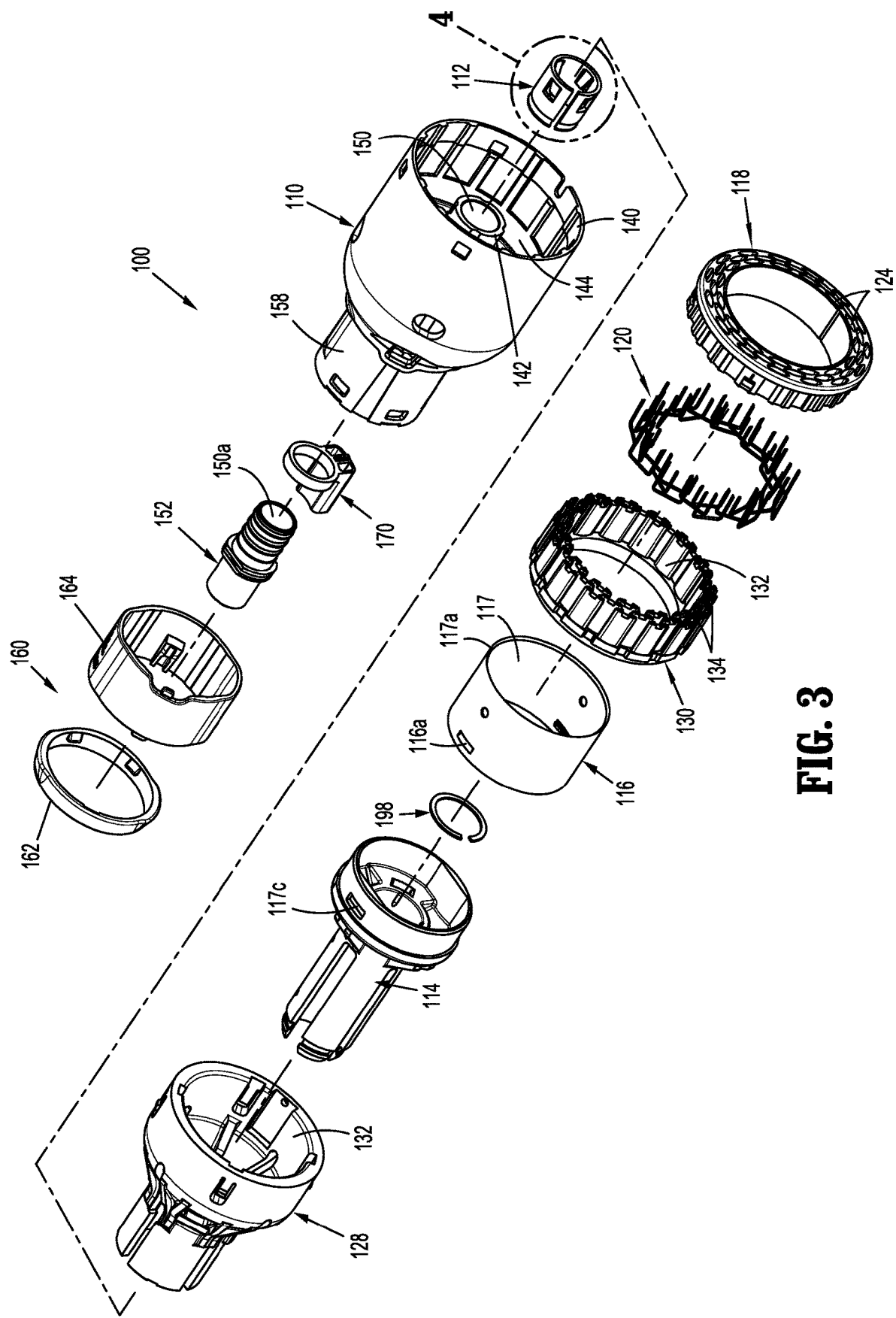
FIG. 3 is an exploded side perspective view of the reload assembly of FIG. 2.

The presently disclosed reload assembly will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

FIGS. 1 and 2 illustrate a circular stapling device 10 including an exemplary embodiment of the presently disclosed reload assembly shown generally as reload assembly 100. The stapling device 10 includes a handle assembly 12, an elongate body or adaptor assembly 14, the reload assembly 100, and an anvil assembly 18 that is supported for movement in relation to the reload assembly 100 between spaced and approximated positions as is known in the art. The reload assembly 100 includes a proximal portion 102 (FIG. 1) that is releasably coupled to a distal portion 14*a* of the elongate body 14. The handle assembly 12 includes a stationary grip 22 that supports actuation buttons 24 for controlling operation of various functions of the stapling device 10 including approximation of the reload and anvil assemblies 100 and 18, respectively, firing of staples from the reload assembly 100, and cutting or coring of tissue.

The stapling device 10 is illustrated as an electrically powered stapling device including an electrically powered handle assembly 12 that may support one or more batteries (not shown). The elongate body 14 is in the form of an adaptor assembly that translates power from the handle assembly 12 to the reload and anvil assemblies 100, 18, respectively. Examples of electrically powered stapling devices can be found in U.S. Pat. No. 9,055,943 (the '943 Patent), U.S. Pat. No. 9,023,014 (the '014 Patent), and U.S. Publication Nos. 2018/0125495, and 2017/0340351 which are incorporated herein by reference in their entirety. Alternately, it is envisioned that the present disclosure could also be incorporated into a manually powered stapling device such as disclosed in U.S. Pat. No. 7,303,106 (the '106 Patent) or a stapling device that is configured for use with a robotic system such as disclosed in U.S. Pat. No. 9,962,159

(the '159 Patent) that does not include a handle assembly. The '106 and '159 Patents are also incorporated herein by reference in their entirety.

Referring to FIG. 3, the reload assembly 100 includes a shell housing 110, a one-way collar 112, a knife carrier 114, an annular knife 116 supported on the knife carrier 114, a staple cartridge 118, a plurality of staples 120 supported within the staple cartridge 118, an annular pusher 128, and a staple pushing member 130. The staple cartridge 118 is annular and defines annular rows of staple pockets 124. Each of the staple pockets 124 supports one of the plurality of staples 120. The annular pusher 128 and the staple pushing member 130 define a longitudinal through bore 132. The pusher 128 has a distal portion that abuts a proximal portion of the staple pushing member 130 such that distal movement of the pusher 128 within the shell housing 110 causes distal movement of the staple pushing member 130. The staple pushing member 130 of the reload 100 has a plurality of fingers 134. Each of the plurality of fingers 134 is received within and is movable through a respective staple pocket 124 of the staple cartridge 118 to eject the staples 120 from the staple pockets 124 when the staple pushing member 130 is moved from a retracted position to an advanced position within the shell housing 110.

The shell housing 110 includes an outer housing portion 140 and an inner housing portion 142 that are spaced from each other to define an annular cavity 144 between the inner and outer housing portions 140 and 142. The annular pusher 128, the pushing member 130, the knife carrier 114, and the annular knife 116 are movable within the annular cavity 144 of the shell housing 110 between retracted and advanced positions. The annular pusher 128 and pushing member 130 are movable independently of the knife carrier 114 and annular knife 116 to eject the staples 120 from the staple cartridge 118. The annular knife 116 is supported about an outer surface of the knife carrier 114 and defines a cylindrical cavity 117 and a distal cutting edge 117a. In embodiments, the knife 116 includes projections 116a (FIG. 3) that are received in openings 117c in the knife carrier 114 to secure the knife 116 about the knife carrier 114. Alternately, other fastening techniques may be used to secure the knife 116 to the knife carrier 114. After the annular pusher 128 and pushing member 130 are moved from their retracted positions to their advanced positions, the knife carrier 114 can be moved from its retracted position to its advanced position to advance the knife 116 to cut tissue positioned radially inward of the staple cartridge 118.

The inner housing portion 142 of the shell housing 110 defines a through bore 150 (FIG. 3) that receives an anvil shaft (not shown) of the anvil assembly 18. For a more detailed description of an exemplary anvil assembly 18, see, e.g., the '106 Patent. The through bore 150 has a proximal portion that receives a bushing 152 that defines a through bore 150a that is coaxial and forms an extension of the through bore 150 of the inner housing portion 142. In embodiments, the bushing 152 is formed of a high strength material, e.g., metal, to provide added strength to the inner housing portion 142 of the shell housing 110. The inner housing portion 142 of the shell housing 110 includes an outer surface that defines an annular recess 159 that has a distal end defined by a stop surface 159a that will be discussed in further detail below.

The shell housing 110 includes a proximal portion 158 (FIG. 3) that supports a coupling mechanism 160 (FIG. 2) that is operable to releasably couple the reload assembly 100 to the adaptor assembly 14 of the stapling device 10 (FIG. 1) to facilitate replacement of the reload assembly 100 and reuse of the stapling device 10. The coupling mechanism 160 includes a retaining member 162 and a coupling member 164. The coupling member 164 is received about the proximal portion 158 of the shell housing 110 and is configured to engage the distal portion 114a (FIG. 1) of the adaptor assembly 14 to couple the adaptor assembly 14 to the reload assembly 100. It is envisioned that other coupling mechanisms can be used to secure the reload assembly 100 to the adaptor 14.

The reload assembly 100 may include an e-prom holder 170 (FIG. 3) that is supported on the shell housing 110 to support an e-prom (not shown). As is known in the art, an e-prom communicates with the adaptor assembly 14 to provide information to the adaptor assembly 14 and the handle assembly 12 related to characteristics of the reload assembly 10.

Figure 4:
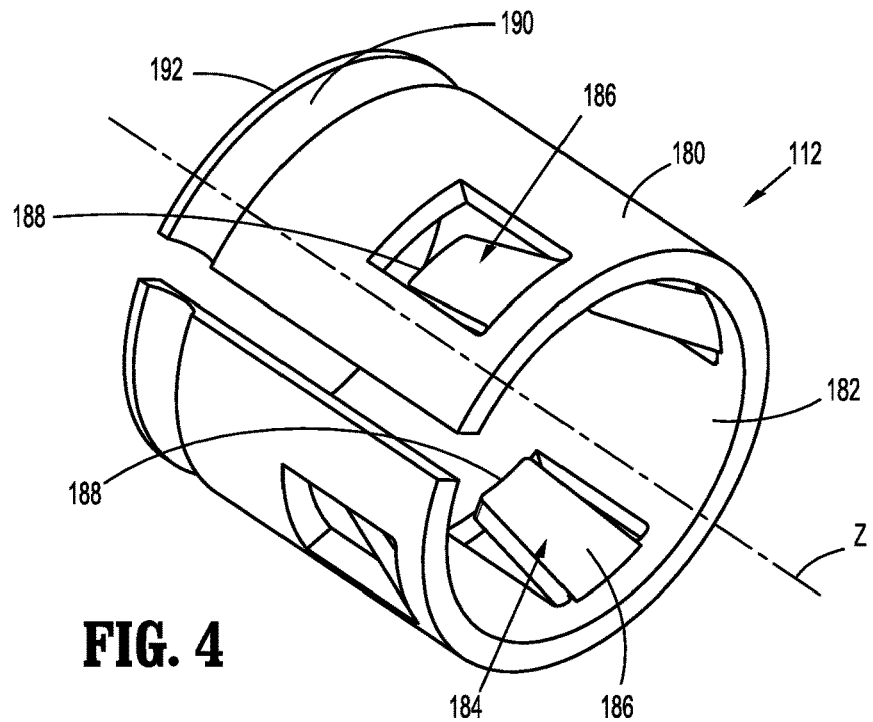
FIG. 4 is an enlarged view of the indicated area of detail shown in FIG. 3.
Figure 5:
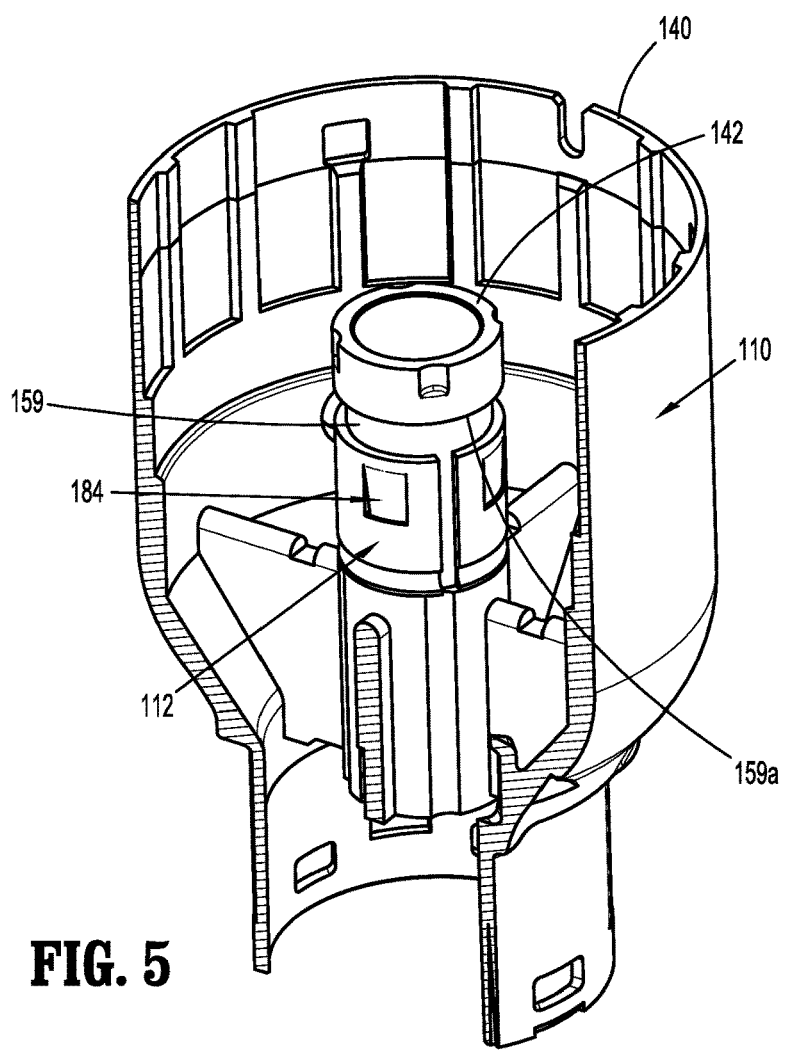
FIG. 5 is a side cross-sectional view of a shell housing of the reload assembly shown in FIG. 3 with a snap-ring of the knife carrier separated from the knife carrier.

Referring to FIGS. 4 and 5, the one-way collar 112 includes a body 180 (FIG. 4) that defines a longitudinal axis "Z" (FIG. 4) and a through bore 182 and is received about the inner housing portion 142 of the shell assembly 110 within the annular recess 159. The body 180 includes at least one directional tang 184 that is configured to allow the one-way collar 112 to move distally within the annular recess 159 but not to move proximally within the annular recess 159. In embodiments, each directional tang 184 includes a cantilevered arm 186 includes a distal end secured to the body 180 of the one-way collar 112 and a proximal end that is positioned within the through bore 182. Each directional tang 184 defines an axis that defines an acute angle with the longitudinal axis "Z" of the body 180 of the one-way collar 112. The proximal end of each of the directional tangs 184 include an edge 188 that engages the inner housing portion 142 to prevent proximal movement of the one-way collar 112 about the inner housing portion 142 of the shell housing 110.

The proximal end of the body 180 of the one-way collar 112 also defines an annular retention groove 190 and a proximal stop surface 192 that is substantially perpendicular to longitudinal axis "Z". In embodiments, the annular retention groove 190 is defined by curved or tapered proximal and distal walls (FIG. 8) and is described in further detail below. In embodiments, the walls or wall defining the annular retention groove 190 may be scalloped or semi-circular in cross-section.

Figure 6:
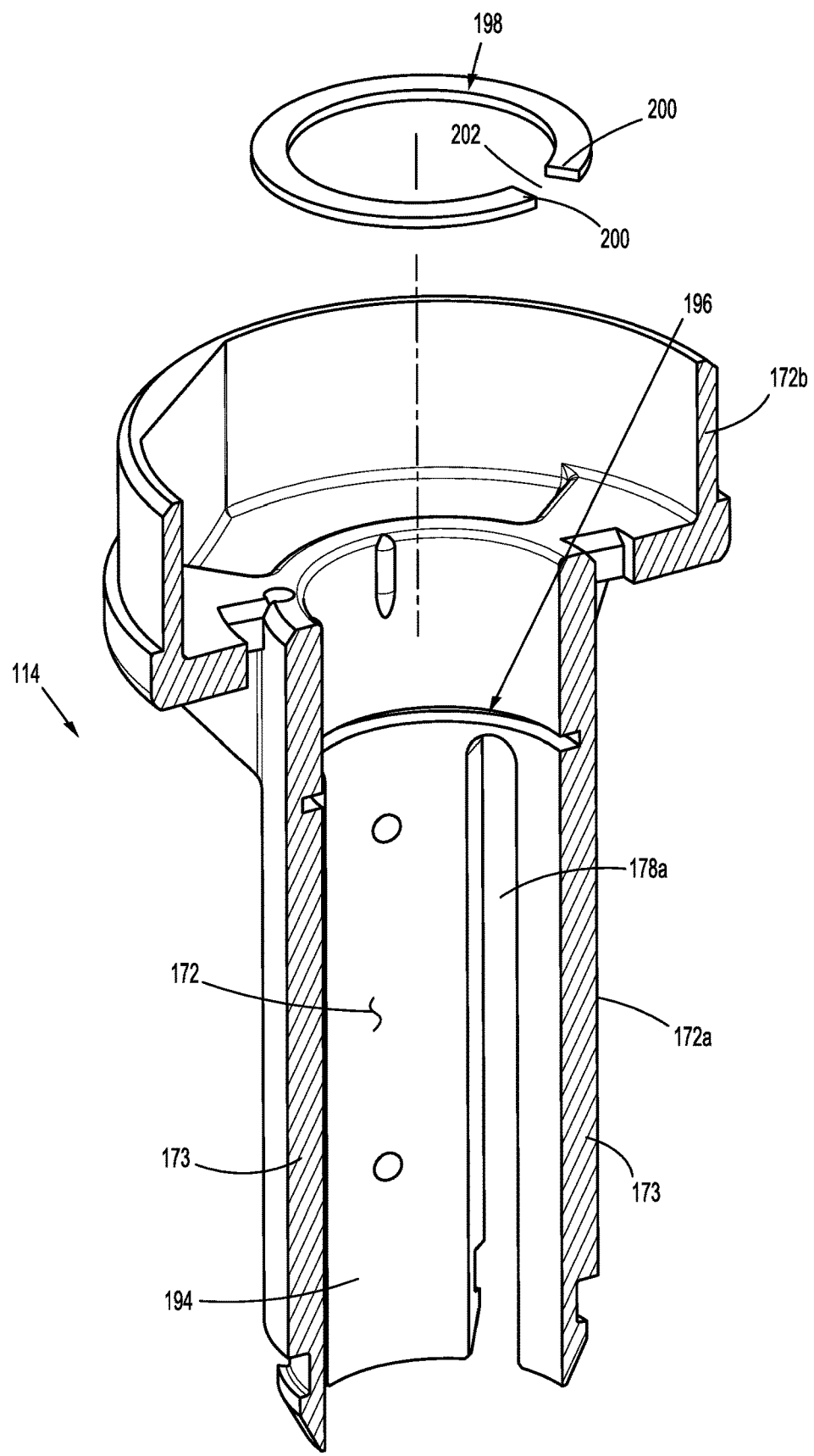
FIG. 6 is a side cross-sectional view of a knife carrier of the reload assembly shown in FIG. 3.
Figure 7:
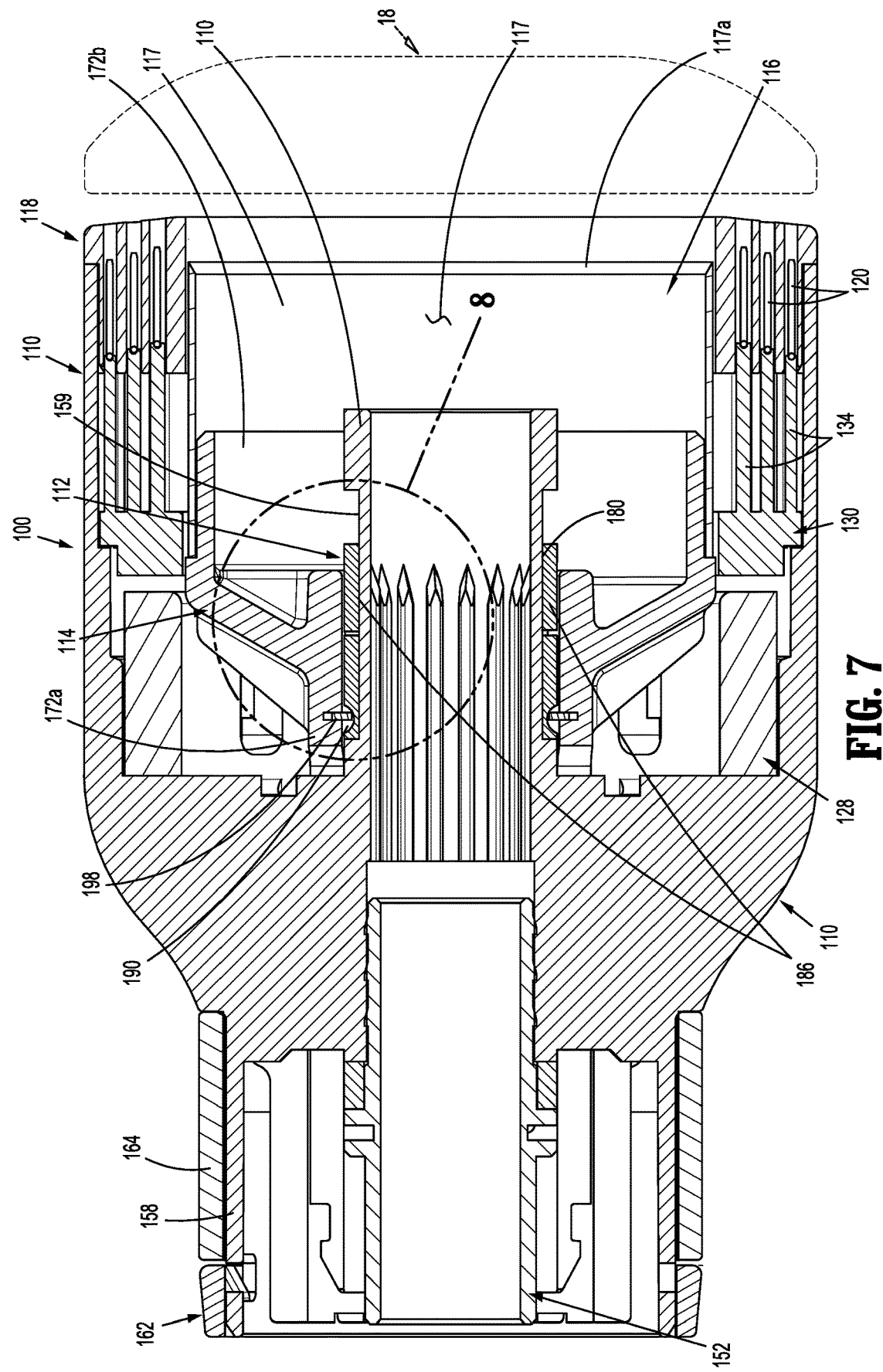
FIG. 7 is a cross-sectional view taken along section line 7-7 of FIG. 2.

Referring to FIGS. 6 and 7, the knife carrier 114 defines a stepped central bore 172 and is movably positioned within the through bore 132 defined by the annular pusher 128 and the pushing member 130 between its retracted and advanced positions. The stepped central bore 172 includes a small diameter proximal portion 172a and a larger diameter distal portion 172b that receives the knife 116. The proximal portion 172a of the central bore 172 of the knife carrier 114 is defined by longitudinally extending body portions 173 that are separated by longitudinal slots 178a and receives the inner housing portion 142 (FIG. 5) of the shell housing 110 such that the knife carrier 114 slides about the inner housing portion 142.

Figure 8:
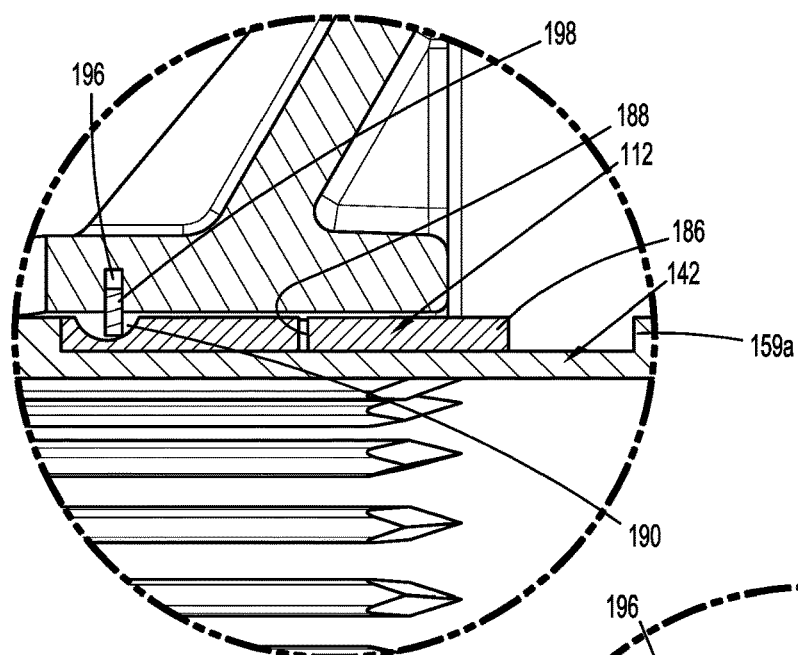
FIG. 8 is an enlarged view of the indicated area of detail shown in FIG. 7 with the reload assembly in a pre-fired position.

Referring also to FIGS. 6 and 8, the inner surface 194 of the knife carrier 114 defines an annular channel 196 that receives a snap-ring 198. The snap-ring 198 is formed of a flexible material and has a semi-circular configuration with first and second ends 200 that are spaced from each other to define a space 202 (FIG. 6). The space 202 between the ends of the snap-ring 198 facilitates deformation of the snap-ring 198 from an unbiased state (FIG. 7) to a biased state (FIG. 11) to allow the outer diameter of the snap-ring 198 to change as described in further detail below.

Referring to FIGS. 7 and 8, when the knife carrier 114 is in a pre-fired retracted position, the snap-ring 198 is positioned within the annular retention groove 190 of the one-way collar 112 and the one-way collar 112 is positioned within the proximal portion of the annular recess 159 of the inner housing portion 142 of the shell housing 110. In this position, the directional tangs 184 of the one-way collar are biased inwardly and maintained in the biased state by the outer surface of the inner housing portion 142 of the shell housing 110. As shown in FIG. 7, the length of the one-way collar 112 is less than the length of the annular recess 159 such that the one-way collar 112 is movable within the annular recess 159 along the inner housing portion 142 of the shell housing 110 between retracted and advanced positions. Engagement between the snap-ring 198 and the one-way collar 112 retains the one-way collar 112 in the retracted position.

Figure 9:
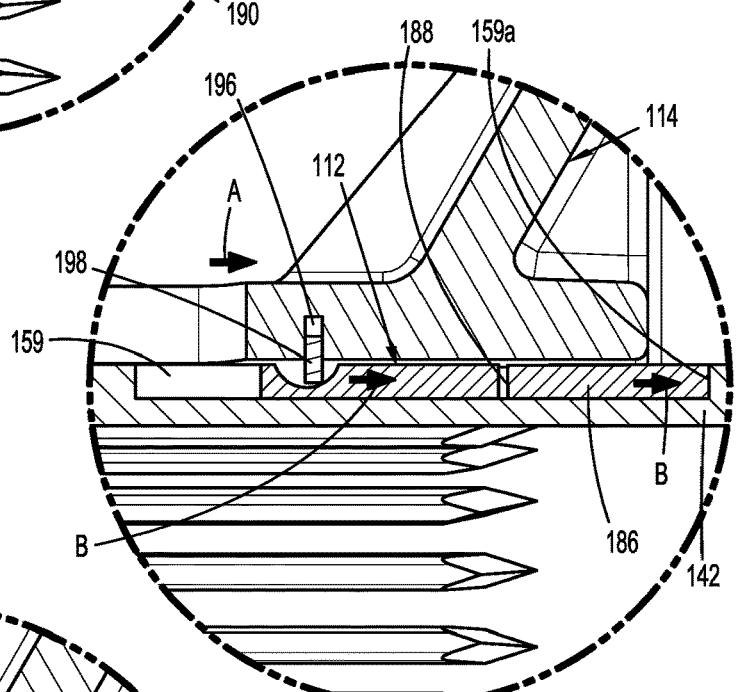
FIG. 9 is an enlarged view of the indicated area of detail shown in FIG. 7 as the knife carrier begins to move from its retracted position towards its advanced position during the firing stroke of the reload assembly.

Referring to FIG. 9, after the annular pusher 128 and the staple pushing member 130 are advanced via actuation of the actuator assembly 14, the knife carrier 114 is advanced from its retracted position towards its advanced position in the direction indicated by arrow "A" to advance the knife 116. When the knife carrier 114 is advanced, engagement between the snap-ring 198 that is supported on the knife carrier 114 and the one-way collar 112 initially causes the one-way collar 112 to move distally within the annular recess 159 defined by the inner housing portion 142 of the shell housing 110 from its retracted position to its advanced position in the direction indicated by arrows "B". When the one-way collar 112 reaches its advanced position, a distal end of the one-way collar 112 engages the stop surface 159a defined by the inner housing portion 142 to prevent further advancement of the one-way collar 112 in relation to the inner housing portion 142.

Figure 10:
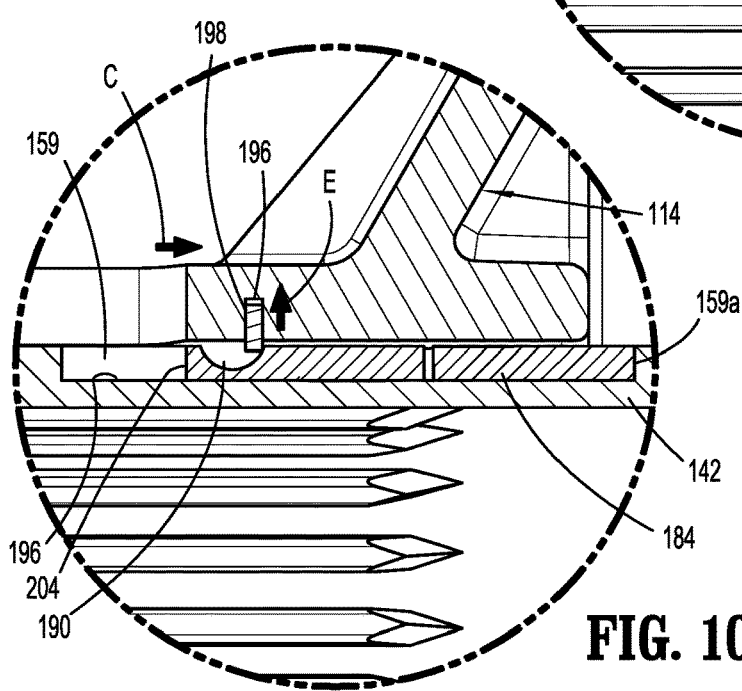
FIG. 10 is an enlarged view of the indicated area of detail shown in FIG. 7 as the knife carrier move further towards its advanced position during the firing stroke of the reload assembly.
Figure 11:
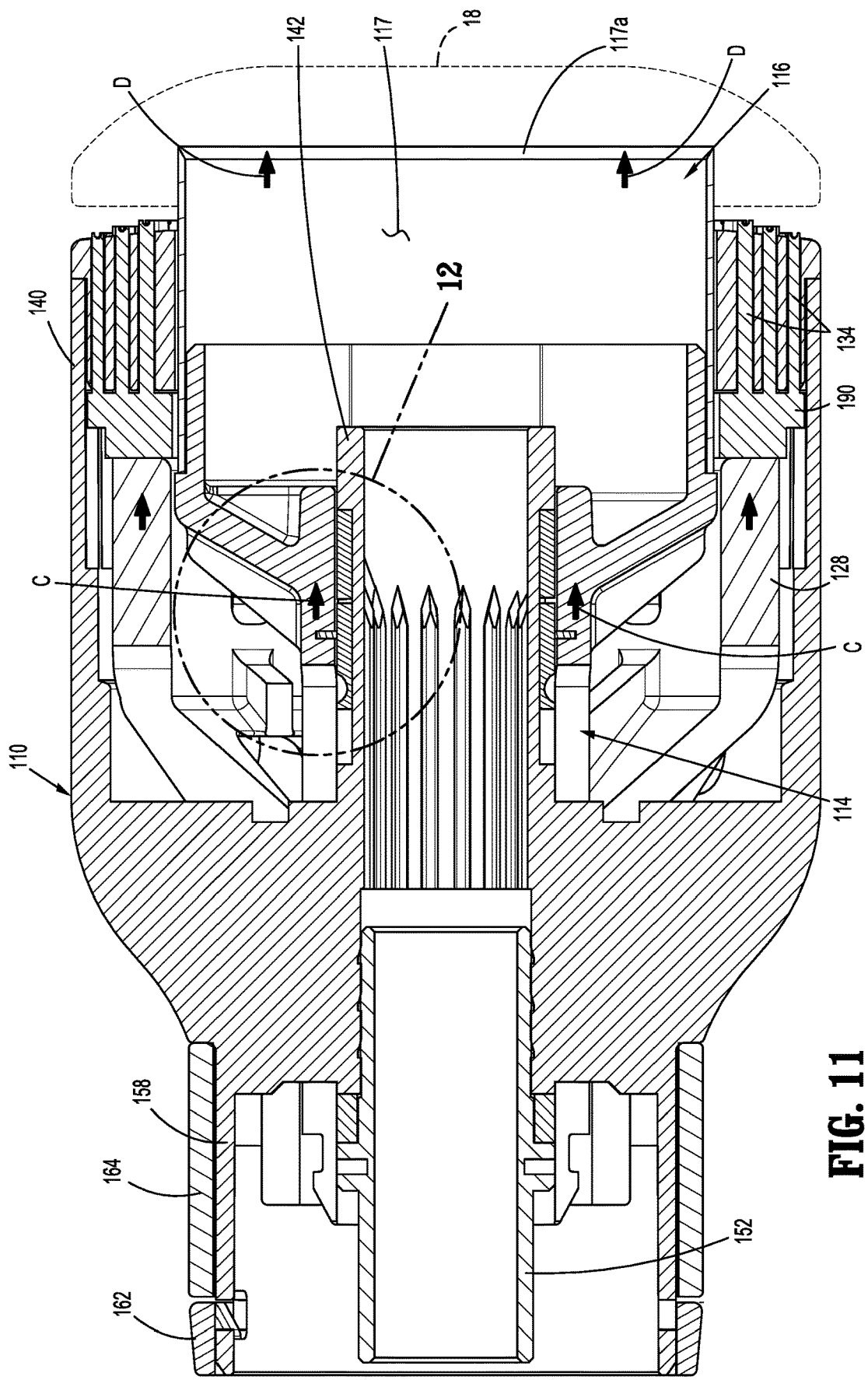
FIG. 11 is a side cross-sectional view of the reload assembly with the knife carrier and the knife in their advanced positions during the firing stroke of the reload assembly.
Figure 12:
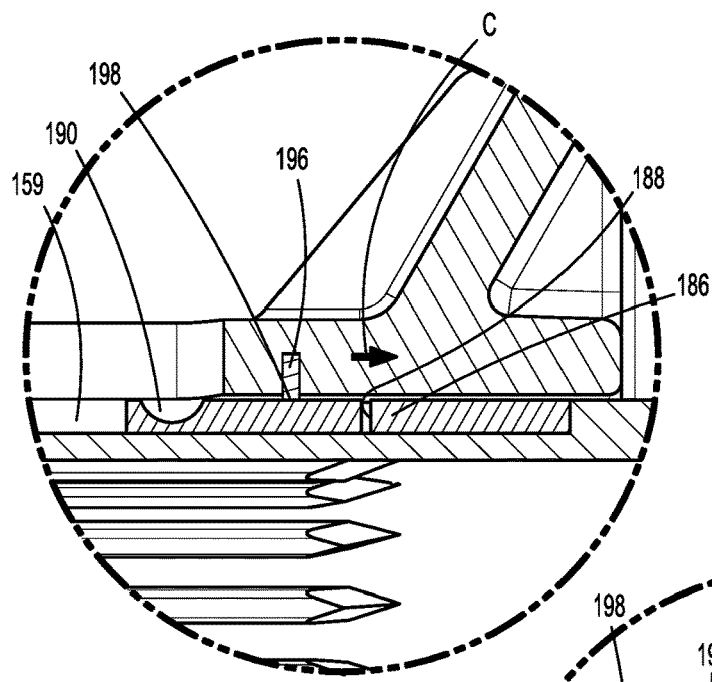
FIG. 12 is an enlarged view of the indicated area of detail shown in FIG. 11 with the knife carrier in its advanced position during the firing stroke of the reload assembly.

Referring to FIGS. 10-12, when the distal end of the one-way collar 112 engages the stop surface 159a (FIG. 10), the knife carrier 114 continues to move towards its advanced position independently of the one-way collar 112 in the direction indicated by arrow "C" to advance the knife 116 in the direction indicated by arrows "D" in FIG. 11. As the knife carrier 114 moves distally in relation to the one-way collar 112, the snap-ring 198 is compressed outwardly in the direction indicated by arrow "E" in FIG. 10 as it moves out of the annular retention groove 190 to a biased state in which the snap-ring 198 slides along an outer surface of the one-way collar 112.

Figure 13:
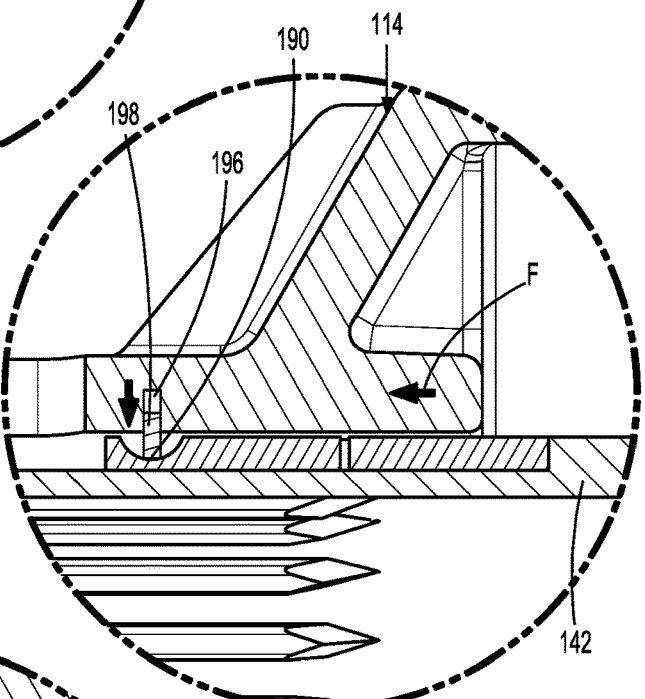
FIG. 13 is an enlarged view of the indicated area of detail shown in FIG. 11 as the knife carrier begins to move from its advanced position back towards its retracted position during the firing stroke of the reload assembly.
Figure 14:
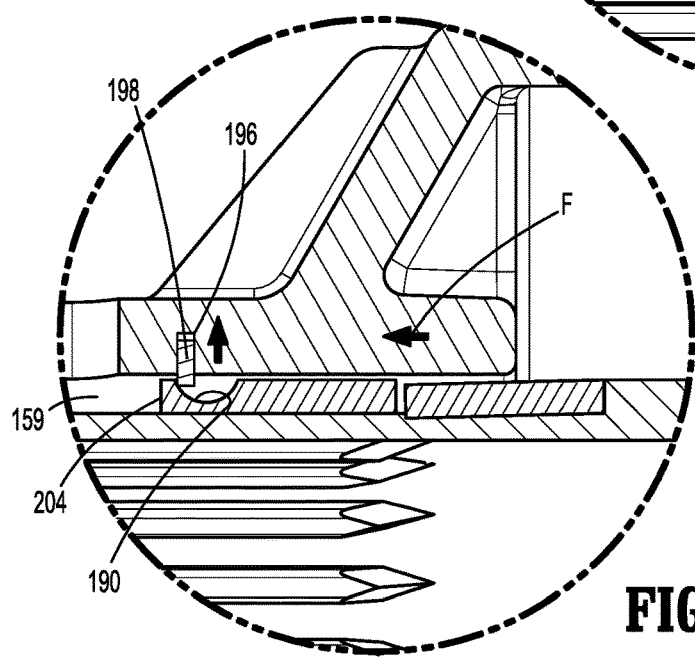
FIG. 14 is an enlarged view of the indicated area of detail shown in FIG. 11 as the knife carrier move further back to its retracted position during the firing stroke of the reload assembly.

Referring to FIGS. 13-16, when the knife carrier 114 is moved from its advanced position (FIG. 12) back towards its retracted position (FIG. 15) in the direction indicated by arrow "F" in FIG. 13, the snap-ring 198 slides along the outer surface of the one-way collar 112 and passes through the annular recess 159 of the one-way collar 112 (FIG. 13). Engagement between the snap-ring 198 and the one-way collar 112 does not cause proximal movement of the one-way collar 112 towards its retracted position because the edges 188 of the cantilevered arms 186 are biased inwardly into engagement with the outer surface of the inner housing portion 142 of the shell housing 110 to prevent proximal movement of the one-way collar. When knife carrier 114 moves to its retracted position as shown in FIG. 15, the snap-ring 198 moves to a position proximally of the one-way collar 112. When this occurs, the snap-ring 198 returns to its unbiased state and moves inwardly to a position proximally of the one-way collar 112 to obstruct movement of the knife carrier 114 back towards its advanced position. In embodiments, a proximal end of the one-way collar 112 defines a stop surface 204 that is substantially perpendicular to the longitudinal axis "Z" of the one-way collar 112 and the snap-ring 198 includes a flat distal face 206 that is positioned to engage the stop surface 204 of the one-way collar 112 to obstruct advancement of the knife carrier 114.

The above-described structure obstructs readvancement of the knife carrier 114 and the knife 116 to safely retain the knife 116 within the shell housing 110 of the reload assembly 100. This minimizes a risk of injury to a clinician during manipulation and disposal of the reload assembly 200.

Although the presently disclosed reload is described in the context of a powered hand instrument, it is to be understood that the presently disclosed reload can be adapted for use with robotically controlled systems as well as hand powered instruments. For example, the reload can be used with an adaptor 14 that is configured to be coupled to a robotically controlled surgical system.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A reload assembly comprising:
a shell housing including an inner housing portion and an outer housing portion, the inner housing portion having an outer surface defining an annular recess;
a staple cartridge supported on a distal portion of the shell housing, the staple cartridge having a plurality of staple pockets, each of the staple pockets receiving a staple;
a pusher supported within the annular recess, the pusher movable between a retracted position and an advanced position to eject the staples from the staple cartridge;
a knife carrier including a body defining a longitudinal axis and supporting a knife, the body of the knife carrier defining a central bore, the inner housing portion of the shell housing being positioned within the central bore of the knife carrier such that the knife carrier is movable about the inner housing portion of the shell housing between advanced and retracted positions;
a resilient snap-ring axially fixed within the central bore of the knife carrier; and
a one-way collar movable within the annular recess of the inner housing portion of the shell housing from a retracted position to an advanced position in response to movement of the knife carrier from its advanced position to its retracted position, wherein the snap-ring is movable to a position proximally of the one-way collar when the one-way collar is in its advanced position to obstruct movement of the knife carrier back towards its advanced position.

2. The reload assembly of claim 1, wherein the one-way collar has an outer surface defining a retention groove, the resilient snap-ring received within the retention groove when the knife carrier and the one-way collar are in their retracted positions.

3. The reload assembly of claim 2, wherein engagement between the snap-ring and the one-way collar causes movement of the one-way collar from its retracted position to its advanced position when the knife carrier moves from its advanced position to its retracted position.

4. The reload assembly of claim 3, wherein the retention groove has a semi-circular configuration.

5. The reload assembly of claim 1, wherein the one-way collar includes a body having at least one directional tang that is configured to prevent proximal movement of the one-way collar about the inner housing portion of the shell housing.

6. The reload assembly of claim 5, wherein each of the at least one directional tangs includes a cantilevered arm having a distal end secured to the body of the one-way collar.

7. The reload assembly of claim 6, wherein the one-way collar defines a through bore and the cantilevered arm of each of the at least one directional tangs includes a proximal edge that is biased towards the through bore of the one-way collar into engagement with the inner housing portion of the shell housing.

8. The reload assembly of claim 7, wherein the at least one directional tang includes a plurality of directional tangs.

9. The reload assembly of claim 2, wherein the annular recess has a proximal end and a distal end and the inner housing portion of the shell housing defines a stop surface at the distal end of the annular recess, the stop surface being positioned to engage the one-way collar to prevent movement of the one-way collar distally of the stop surface.

10. The reload assembly of claim 1, wherein the one-way collar includes a proximal end defining a stop surface, the stop surface positioned to engage the snap-ring when the one-way collar is in its advanced position and the knife carrier is in its retracted position to prevent readvancement of the knife carrier.

11. A circular stapling device comprising;
an elongate body having a proximal portion and a distal portion; and
a reload assembly supported on the distal portion of the elongate body, the reload assembly including:
a shell housing including an inner housing portion and an outer housing portion, the inner housing portion having an outer surface defining an annular recess;
a staple cartridge supported on a distal portion of the shell housing, the staple cartridge having a plurality of staple pockets, each of the staple pockets receiving a staple;
a pusher supported within the annular recess, the pusher movable between a retracted position and an advanced position to eject the staples from the staple cartridge;
a knife carrier including a body defining a longitudinal axis and supporting a knife, the body of the knife carrier defining a central bore, the inner housing portion of the shell housing being positioned within the central bore of the knife carrier such that the knife carrier is movable about the inner housing portion of the shell housing between advanced and retracted positions;
a resilient snap-ring axially fixed within the central bore of the knife carrier; and
a one-way collar movable within the annular recess of the inner housing portion of the shell housing from a retracted position to an advanced position in response to movement of the knife carrier from its advanced position to its retracted position, wherein the snap-ring is movable to a position proximally of the one-way collar when the one-way collar is in its advanced position to obstruct movement of the knife carrier back to its advanced position.

12. The circular stapling device of claim 11, wherein the one-way collar has an outer surface defining a retention groove, the resilient snap-ring received within the retention groove when the knife carrier and the one-way collar are in their retracted positions.

13. The circular stapling device of claim 12, wherein engagement between the snap-ring and the one-way collar causes movement of the one-way collar from its retracted position to its advanced position when the knife carrier moves from its advanced position to its retracted position.

14. The circular stapling device of claim 13, wherein the retention groove has a semi-circular configuration.

15. The circular stapling device of claim 11, wherein the one-way collar includes a body having at least one directional tang that is configured to prevent proximal movement of the one-way collar about the inner housing portion of the shell housing.

16. The circular stapling device of claim 15, wherein each of the at least one directional tangs includes a cantilevered arm having a distal end secured to the body of the one-way collar.

17. The circular stapling device of claim 16, wherein the one-way collar defines a through bore and the cantilevered arm of each of the at least one directional tangs includes a proximal edge that is biased towards the through bore of the one-way collar into engagement with the inner housing portion of the shell housing.

18. The circular stapling device of claim 17, wherein the at least one directional tang includes a plurality of directional tangs.

19. The circular stapling device of claim 18, wherein the annular recess has a proximal end and a distal end, and the inner housing portion of the shell housing defines a stop surface at the distal end of the annular recess, the stop surface being positioned to engage the one-way collar to prevent distal movement of the one-way collar distally of the stop surface.

20. The circular stapling device of claim 11, wherein the one-way collar includes a proximal end defining a stop surface, the stop surface positioned to engage the snap-ring when the one-way collar is in its advanced position and the knife carrier is in its retracted position to prevent readvancement of the knife carrier.

* * * * *